United States Patent [19]

Miller

[11] Patent Number: 5,423,844
[45] Date of Patent: Jun. 13, 1995

[54] ROTARY SURGICAL CUTTING INSTRUMENT

[75] Inventor: Michael E. Miller, Indianapolis, Ind.

[73] Assignee: Promex, Inc., Indianapolis, Ind.

[21] Appl. No.: 141,405

[22] Filed: Oct. 22, 1993

[51] Int. Cl.⁶ .............................................. A61B 17/32
[52] U.S. Cl. ..................................... 606/171; 128/751
[58] Field of Search ............... 606/159, 167, 170, 171, 606/180; 604/22; 128/751, 752

[56] References Cited

U.S. PATENT DOCUMENTS

| | | | |
|---|---|---|---|
| 3,289,669 | 12/1966 | Dwyer et al. | 128/752 |
| 3,815,604 | 6/1974 | O'Malley et al. | 606/171 |
| 4,011,869 | 3/1977 | Seiler, Jr. | |
| 4,203,444 | 5/1980 | Bonnell et al. | 606/170 |
| 4,512,344 | 4/1985 | Barber | 606/170 |
| 4,819,635 | 4/1989 | Shapiro | 606/170 |
| 4,867,157 | 9/1989 | McGurk-Burleson et al. | 606/180 |
| 5,106,364 | 4/1992 | Hayafuji et al. | 604/22 |
| 5,152,744 | 10/1992 | Krause et al. | 606/170 |
| 5,226,910 | 7/1993 | Kajiyama et al. | 604/22 |
| 5,242,460 | 9/1993 | Klein et al. | 606/180 |

FOREIGN PATENT DOCUMENTS

| | | | |
|---|---|---|---|
| 3828478 | 5/1989 | Germany | 606/170 |
| 2205045 | 11/1988 | United Kingdom | 606/170 |
| 1454457 | 1/1989 | U.S.S.R. | 604/22 |
| 9208416 | 5/1992 | WIPO | 606/170 |

*Primary Examiner*—Stephen C. Pellegrino
*Assistant Examiner*—Nancy Mulcare
*Attorney, Agent, or Firm*—Woodard, Emhardt, Naughton Moriarty & McNett

[57] ABSTRACT

A rotary surgical cutting instrument for use in cutting tissue within an anatomical space includes an outer cannula sized for percutaneous insertion into the anatomical space. The outer cannula defines a central bore along the length of the outer cannula and a cutting opening adjacent the distal end sized to receive tissue therethrough. A rotatably driven tubular cutting member is disposed within the central bore of the outer cannula, with a cutting edge rotating beneath the cutting opening of the cannula. The cutting edge extends at least substantially completely circumferentially around the tubular cutting head and circumscribes an angle relative to longitudinal and radial planes defined by the outer cannula. The cutting member can include a tubular cutting head and body portion that are connected by a hinge to permit pivoting of the cutting head relative to the body. The cutting member is formed from a flat sheet that is wound into a tubular shape within the outer cannula with opposite first and second edges adjacent each other. The cutting edge extends at an oblique angle between the first and second edges. The cutting edge is defined in the sheet at an oblique angle extending between the first and second edges. In one embodiment, the cutting head and body are formed by separate sheet portions attached by the hinge, the cutting head being formed from a trapezoidal sheet. In another embodiment, the cutting head and body are formed from one sheet.

5 Claims, 1 Drawing Sheet

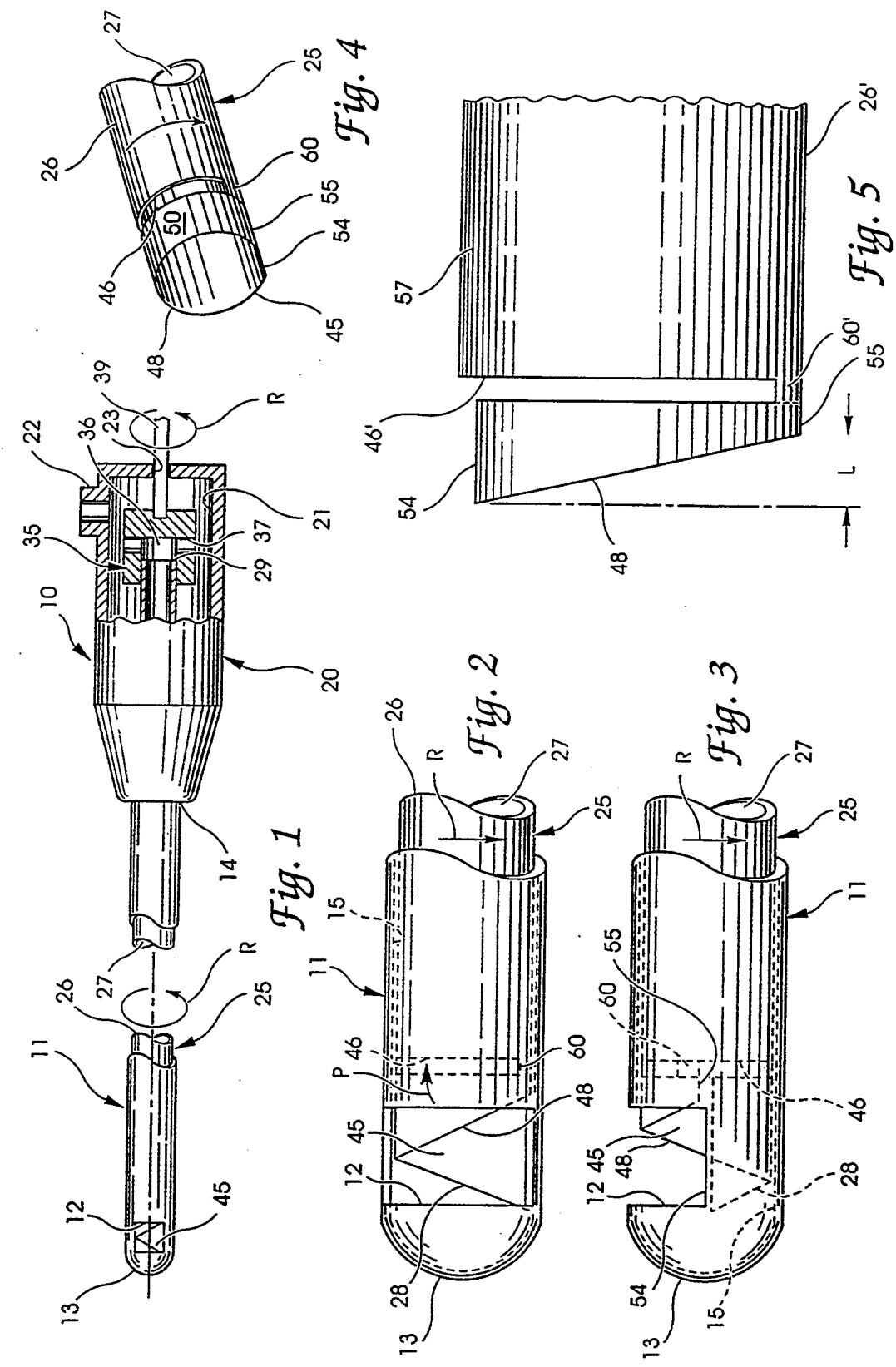

ROTARY SURGICAL CUTTING INSTRUMENT

BACKGROUND OF THE INVENTION

The present invention relates to a percutaneous surgical instrument for the excision and removal of a wide range of tissues. More particularly, the invention resides in a rotary cutting instrument that is particularly well suited for operation at a broad range of rotational speeds, and which is capable of cutting tough tissue, such as may be encountered during orthopedic or spinal surgery. Although the present invention has application in many surgical procedures, the following disclosure will pertain principally to minimally invasive cutting instruments used in the field of spinal surgery.

In the field of spinal surgery, one problem that is frequently diagnosed and treated concerns degeneration or herniation of an intervertebral disk. Treatment of these diagnosed conditions often requires some degree of fusion between the adjacent vertebrae serviced by the affected intervertebral disk. In spinal fusion procedures of this type, it is typical to entirely remove the affected disk for replacement by bone graft material, or in some cases, by a prosthetic disk.

Within the last decade, techniques for percutaneous diskectomies have been developed in which the disk tissue is removed by a cutting instrument inserted percutaneously. These techniques have virtually eliminated the need for highly invasive surgical procedures to remove disk tissue. One such system is described in the patent to Onik, U.S. reissue Pat. No. 33,258, which shows a "tube within a tube" cutting instrument. The device disclosed in the Onik patent incorporates a rotary inner cutting sleeve operated within the central bore of an outer cutting sleeve.

Another instrument for percutaneous tissue removal is shown in the patent to Bonnell et al., No. 4,203,444. The Bonnell device is of the rotary genre in which an internal blade rotates within an outer cannula having a side facing shaving port. In the Bonnell device, along with other rotary cutters of this type, the axial edges of the shaving port coact with the axial extending edges of the internal blade in a scissors-type action to shear tissue. The internal blade is hollow to allow the tissue shavings to be aspirated through the instrument during the cutting operation. Rotary cutters of this type are often susceptible to becoming clogged as the excised tissue spools around the internal rotary blade, thereby clogging the aspiration channel or even stalling the rotation of the cutting blade.

Another problem common among both rotary and linearly reciprocating devices is an inability to cut very tough tissue using a percutaneous cutting device. Certainly, larger cutting instruments driven by larger motors are capable of cutting very tough or hard tissue. However, no prior device has been able to avoid the trade-off that is forced between a minimally invasive cutting instrument and the ability to cut a variety of tough tissues without clogging or stalling the cutting instrument.

Another disadvantage experienced particularly by the rotary devices is the need for an outer cannula having a shaving port that includes a sharp edge to assist in the cutting or shaving operation. This typically necessitates a rigid cutting instrument, such as the Bonnell device. This requirement in turn limits the environment in which a percutaneous cutter of this design can be utilized because the external tube or cannula is not flexible enough to be bent or guided around anatomic features, as may be required in many spinal surgical procedures.

There is therefore a need in the field of tissue excision and removal for a surgical cutter that is well suited for minimally invasive uses, yet that is still capable of cutting the tough tissues encountered in spinal and orthopedic procedures. The cutting instrument must be capable of excising the tissue cleanly without tearing, and of aspirating the tissue pieces efficiently and without clogging. The instrument should further be flexible to allow both the outer tube and the inner tube to bend as required to reach the cutting site. These and other needs are addressed by the present invention.

SUMMARY OF THE INVENTION

The present invention contemplates a rotary surgical cutting instrument for use in cutting tissue within an anatomical space having an outer cannula sized for percutaneous insertion into the anatomical space. The outer cannula defines a central bore along the length of the outer cannula and a cutting operating adjacent the distal end sized to receive tissue therethrough. The cannula is supported at is proximal end by a handpiece. A cutting member is rotatably disposed within the central bore of the outer cannula, with a tubular cutting head having a cutting edge rotating beneath the cutting opening of the cannula. The cutting edge extends at least substantially completely circumferentially around the tubular cutting head and circumscribes an angle relative to longitudinal and radial planes defined by the outer cannula.

The cutting member is connected to a motor or other source of rotary motion to rotate the cutting head within the outer cannula so that the cutting edge traverses the cutting opening in the outer cannula, severing tissue drawing therein by suction applied through the cutting member. The cutting member can include a tubular cutting head and body portion that are connected by a hinge to permit pivoting of the cutting head relative to the body. When the cutting edge contacts tissue within the outer cannula the cutting head pivots about the hinge so the cutting edge moves closer to the cutting opening, leading to essentially a zero clearance between the cutting edge and the outer cannula to more clearly and efficiently sever tissue within the cutting opening.

In one aspect of the invention, the cutting member is formed from a flat sheet that is wound into a tubular shape within the outer cannula. The flat sheet has opposite first and second edges that are adjacent each other when the sheet is wound into its tubular shape. In one embodiment, the cutting edge is defined in the sheet at an oblique angle extending between the first and second edges. In another embodiment, the cutting head and body are formed by separate sheet portions attached by the hinge. The cutting head is formed from a trapezoidal sheet with the cutting edge extending at an oblique angle between the first and second edges.

One object of the present invention is to provide a rotary surgical cutting instrument that efficiently and quickly severs tissue within an anatomical space for aspiration into a collection container. A further object is to produce a rotary cutting instrument that is easily and inexpensively produced, yet that still yields superior cutting results.

One benefit of the rotary surgical cutting instrument of the present invention is that it provides a cutting edge that extends substantially completely circumferentially to generate a slicing, rather than a chopping, action to excise tissue. Another benefit of the inventive instrument is that it opens and closes the cutting opening to effectively draw perfectly sized portion of tissue into the acting opening.

Other objects and benefits of the present invention will become apparent upon consideration of the following written description and accompanying figures.

BRIEF DESCRIPTION OF THE DRAWINGS

FIG. 1 is a partial cutaway side view of the rotary surgical cutting instrument in accordance with one embodiment of the present invention.

FIG. 2 is an enlarged top cutaway view of the end of the cutting instrument shown in FIG. 1.

FIG. 3 is an enlarged side cutaway view of the end of the cutting instrument shown in FIG. 1.

FIG. 4 is a cutaway view of the cutting blade forming part of the surgical cutting instrument depicted in FIG. 1.

FIG. 5 is a top plan view of the cutting blade similar to the blade shown in FIG. 4 shown the blade sheet prior to forming into the rotary blade.

DESCRIPTION OF THE PREFERRED EMBODIMENTS

For the purposes of promoting an understanding of the principles of the invention, reference will now be made to the embodiment illustrated in the drawings and specific language will be used to describe the same. It will nevertheless be understood that no limitation of the scope of the invention is thereby intended, such alterations and further modifications in the illustrated device, and such further applications of the principles of the invention as illustrated therein being contemplated as would normally occur to one skilled in the art to which the invention relates.

Referring first to FIG. 1, a surgical cutting instrument 10 is shown which includes an outer cannula 11. The outer cannula 11 includes a tissue opening 12 defined near its distal end 13. Preferably, the distal end 13 is rounded or blunt to minimize trauma during the introduction of the cutting instrument 10 into the surgical cutting site. The outer cannula 11 defines a bore 15 from its distal end 13 to its proximal end 14.

The cutting instrument 10 further includes a handpiece 20 which is configured to be grasped by the surgeon to support the instrument. The outer cannula 11 is engaged to the handpiece 20 at the proximal end 14 of the cannula. The handpiece 20 is generally hollow and defines an aspiration chamber 21 therein with an aspiration fitting 22 extending from the handpiece to provide a location for engaging an aspiration tube. Tissue is drawn into tissue opening 12 by application of suction at the fitting 22. The excised tissue passes through the aspiration chamber 21 and the aspiration fitting 22 into a suitable container, as is known in the art. The end of the handpiece 20 defines a drive shaft bore 23 which receives a drive shaft therethrough as disclosed herein.

As thus far described, the surgical cutting instrument 10 incorporates many features common to both rotary and reciprocating devices of the prior art. One exception, however, is that the tissue opening 12 does not incorporate or require a cutting edge. This exception allows the outer cannula 11 to be formed of a flexible material so that the outer cannula can be steered or bent around portions of the spine to reach an appropriate location for resection of disk material. Thus, the outer cannula 11 can be formed of a flexible biocompatible plastic and need not be formed of metal as with prior devices.

In a further aspect of the invention, the surgical cutting instrument 10 includes a unique inner cutting member 25. The inner cutting member 25 includes a tubular body 26 having an aspiration passageway 27 defined therethrough from its distal end 28 to its proximal end 29. As shown more clearly in FIGS. 2 and 3, the distal end 28 resides adjacent the tissue opening 12 of the outer cannula 11. The proximal end 29 is engaged within an interface bore 36 of a drive fitting 35. The drive fitting 35 includes number of aspiration bores 37, which provide fluid communication between the aspiration passageway 36 of the inner cutting member 25 to the aspiration chamber 21 of the handpiece 20. Thus, tissue fragments sliced by the subject tissue by the inner cutting member 25 can be drawn along the aspiration passageway 27, through the handpiece 20, out the aspiration fitting 22 and into a collection chamber by an appropriate suction source.

A drive shaft 39 is engaged to the drive fitting 35 and extends through the shaft bore 13 in the handpiece 20. The drive shaft 39 is engaged to a conventional rotary motor to provide rotational motion of the shaft and the inner cutting member 25 in the direction of the arrow R in FIGS. 1-3. The handpiece 20 is preferably configured to a rotary motor, although a flexible drive shaft connection to a remote motor is also contemplated.

The inner cutting member 25 includes a cutting head portion 45 disposed to essentially overlap the cutting opening 12 of the outer cannula 11. The cutting head portion 45 extends circumferentially around the bore 15 of the outer cannula 11 as shown in FIGS. 2 and 3. A slot 46 is defined between the tubular body 26 and the cutting head 45 which allows the cutting head to flex or pivot in the direction of the arrow P toward the tubular body 26 as tissue is excised. In particular, the cutting head portion 45 includes a cutting edge 48 which contacts and presses against the tissue as the inner cutting member 25 is rotated in the direction of the arrow R. As the cutting edge 48 contacts the tissue, a reaction force is exerted against the edge 48 by the tissue which is generally in the direction of the arrow P shown in FIG. 2. The force in this direction in essence closes the portion of the slot 46 as the cutting head portion 45 is urged toward the tubular body 26. The cutting head portion 45 is attached to the tubular body 26 by way of a hinge 60. This hinge 60 hingedly connects the cutting head portion 45 to the body so that the head portion 45 flexes in the direction of the arrow P. This flexing or pivoting action allows the cutting edge 48 of the cutting head portion 45 to remain in contact with the bore 15 of the outer cannula 11 which, in turn, adds rigidity to the cutting edge 48 to enhance the ability of the cutting head portion 45 to slide the subject tissue.

In rotary cutting devices of the prior art, the inner cutting member is generally tubular in shape, including the cutting head portion. However, the present invention contemplates that at least the cutting head portion 45 is formed by a trapezoidal-shaped sheet 50, as shown in FIGS. 4 and 5. This sheet 50 includes opposite edges 54 and 55 which are oriented along the longitudinal length of the inner cutting member 25, as shown in FIGS. 2-4, with the cutting edge 48 oriented at an oblique angle to both edges 54 and 55. As depicted most clearly in FIG. 3, the edges 54 and 55 do not contact and are not engaged to each other when the sheet is wound into a tubular shape so that the cutting head portion 45 is circumferentially discontinuous.

In the preferred embodiment, the trapezoidal sheet 50, which defines the cutting head portion 45, is composed of a thin metal, preferably the thickness will be a function of the diameter of the cutter. Thus, this cutting head portion, and particularly the cutting edge 48, is similar to a razor blade. When the portion 45 is wound into a tubular shape, the cutting edge 48 circumscribes an angle substantially completely circumferential edge relative to longitudinal and radial planes defined by the outer cannula 11. With this thin, sharp trapezoidal sheet 50 and cutting edge 48, it is possible to easily slide tissue as the surgical cutting instrument 10 is placed in contact with the subject tissue. Simply by rotation of the inner cutting member 25, the cutting edge 48 slides against and slices through tissue drawn into the cutting opening 12 of the outer cannula 11 by way of suction applied to the aspiration fitting 22 of the handpiece 20. Viewed in another manner, rotation of the cutting head 45 with the angled cutting edge 48 causes the edge 48 to gradually close the opening 12 as more of the aligned cutting head portion 45 is exposed to the opening 12. In this respect, the slicing action provided by the cutting head portion 45 obviates the need for a cooperating shearing surface on the cutting opening 12 of the outer cannula 11.

As may be discerned from the figures, as the blade continues to rotate, the cutting edge 48 effective "disappears" beyond the distal edge of the cutting opening 12, only to suddenly reappear as the first edge 54 passes beneath the opening 12. This angled cutting edge, thus, continuously opens and closes the cutting opening 12, which enhances the cutting instrument's ability to draw, or "tease" tissue into the instrument. The strength for the cutting head portion 45 is provided by wrapping the sheet 50 within the bore 15 of the outer cannula 11 such that the cutting head portion is supported and maintained in its circumferential shape by the outer cannula.

In the preferred embodiment, only the cutting head portion 45 is formed by a trapezoidal sheet 50. The tubular body 26 of the inner cutting member 25 is a separate complete tubular piece as shown in FIG. 4. The tubular body 26 includes the mounting hinge 60 projecting from one end to which the trapezoidal sheet 50 is attached. Specifically, the smaller section edge 55 of the sheet 50 is affixed to the mounting hinge 60, such as by welding or soldering. It can thus be seen that the tubular body 26 of the inner cutting member 25 can be a thicker walled component to provide strength. The tubular body 20 is then engaged to the drive fitting 35 to transmit the rotational motion from the drive shaft 39 to the cutting head portion 45.

Alternatively, as shown in FIG. 5, an inner cutting member 25' can include a second sheet 52 which is wound into the form of a tubular body 26, in this alternative embodiment, the trapezoidal sheet 50 and the flat sheet 52 are cut from a single piece of stock material. The mounting hinge 60' is then integral between the trapezoidal sheet 50 and the flat sheet 52, thereby defining a slot 46' between the two. The composite sheet is then wound in to a cylindrical form and inserted into the bore 15 of the outer cannula 11. The flat sheet 52 may also include an overlap margin 57 which allows the tubular body 26' to assume a fully circumferential configuration. The overlap margin 57 can be suitably soldered or welded to form a continuous cylindrical shape for the tubular body 26.

In accordance with the present invention, the surgical cutting instrument 10 incorporates the "tube within a tube" approach. The outer cannula 11, as well as the tubular body 26 of the inner cutting member 25, are preferably formed of a flexible material, such as a medical grade plastic. In this manner, the instrument 10 is well suited for being bent or guided through a body passageway to a cutting site. On the other hand, the cutting head portion 45 of the inner cutting member 25 is preferably formed of a medical grade metal, such as stainless steel. The thin cutting edge 48 of the cutting head portion 45, as well as the inherent rigidity provided by rotation of the head portion 45 within the bore 15 of the outer cannula 11, allows the instrument 10 to operate in a slicing manner rather than in a scissors manner, as with previous rotary cutters.

It has been found that the surgical cutting instrument 10 can be operated at a wide range of rotational speeds, such as from 60 rpm to 2,000 rpm. Since the cutting head portion 45 rotates against the bore 15 of the outer cannula 11, one limitation in the rotational speed is the temperature increase generated by the friction between the blade and the outer cannula. With respect to the tubular body 26, the friction problem can be reduced by forming the outer cannula 11 and the tubular body 26 of a non-metallic material. The friction between the cutting blade 45 and the outer cannula 11 is also reduced if the outer cannula is formed of a non-metallic material.

While the invention has been illustrated and described in detail in the drawings and foregoing description, the same is to be considered as illustrative and not restrictive in character, it being understood that only the preferred embodiment has been shown and described and that all changes and modifications that come within the spirit of the invention are desired to be protected.

What is claimed is:

1. A surgical cutting instrument for use in cutting body tissue comprising:
    an outer cannula defining a central bore along the length of said outer cannula and having a proximal end and a distal end, said outer cannula further defining a cutting opening adjacent said distal end sized to receive tissue therethrough;
    a handpiece supporting said outer cannula at said proximal end;
    a cutting member rotatably disposed within said central bore of said outer cannula with a distal end adjacent said cutting opening, said cutting member including a tubular cutting head portion at its distal end, said cutting head portion having an end opening defining a cutting edge substantially entirely around said end opening, wherein said cutting edge circumscribes an angle relative to longitudinal and radial planes defined by said outer cannula; and
    connecting means within said handpiece for connecting said cutting member to a source of rotary motion to rotate said cutting head portion within said outer cannula so that said cutting edge traverses said cutting opening in said outer cannula,
    wherein said cutting head portion is a flat trapezoidal sheet having a first edge and an opposite second edge with said cutting edge extending at an oblique angle between said first and second edges, said sheet wound into a tubular form within said outer cannula with said first edge adjacent said second edge, whereby as said cutting head portion rotates within said outer cannula, said cutting edge opens and closes said cutting opening to continuously sever tissue drawn therein.

2. The surgical cutting instrument of claim 1, wherein said cutting member further includes;

a tubular body portion connected to said cutting head portion; and means for fluidly connecting said tubular body portion to a suction source to provide suction through said tubular body portion to aspirate tissue therethrough severed by said cutting head portion.

3. The surgical cutting instrument of claim 2, wherein said cutting member includes a hinge portion connecting said cutting head portion with said body portion to permit pivoting of said cutting head portion relative to said body portion, whereby said cutting head portion pivots about said hinge portion toward said cutting opening when said cutting head contacts tissue within said outer cannula.

4. The surgical cutting instrument of claim 2, wherein said cutting member is a flat sheet having a trapezoidal portion defining said cutting head portion.

5. The surgical cutting instrument of claim 4, wherein said flat sheet includes a rectangular portion defining said tubular body portion when said sheet is wound into a tubular form, and a hinge portion connecting said rectangular portion to said trapezoidal portion.

* * * * *

UNITED STATES PATENT AND TRADEMARK OFFICE
CERTIFICATE OF CORRECTION

PATENT NO. : 5,423,844
DATED : June 13, 1995
INVENTOR(S) : Michael E. Miller

It is certified that error appears in the above-identified patent and that said Letters Patent is hereby corrected as shown below:

Column 3, line 8, please change "acting" to "cutting";

Column 3, line 25, please change "shown" to "showing".

Signed and Sealed this

Fourteenth Day of November, 1995

*Attest:*

BRUCE LEHMAN

*Attesting Officer*     *Commissioner of Patents and Trademarks*